(12) United States Patent
Palazzo et al.

(10) Patent No.: US 11,268,941 B2
(45) Date of Patent: *Mar. 8, 2022

(54) COOKING OIL FILTRATION TRANSPORT APPARATUS WITH OIL QUALITY SENSOR

(71) Applicant: Frontline International, Inc., Cuyahoga Falls, OH (US)

(72) Inventors: John W. Palazzo, Akron, OH (US); Giovanni Brienza, Copley, OH (US)

(73) Assignee: FRONTLINE INIERNATIONAL, INC., Cuyahoga Falls, OH (US)

( * ) Notice: Subject to any disclaimer, the term of this patent is extended or adjusted under 35 U.S.C. 154(b) by 190 days.

This patent is subject to a terminal disclaimer.

(21) Appl. No.: 16/358,599

(22) Filed: Mar. 19, 2019

(65) Prior Publication Data

US 2020/0300830 A1    Sep. 24, 2020

(51) Int. Cl.
*G01N 33/03* (2006.01)
*A47J 37/12* (2006.01)
*G01N 27/22* (2006.01)

(52) U.S. Cl.
CPC .......... *G01N 33/03* (2013.01); *A47J 37/1223* (2013.01); *A47J 37/1271* (2013.01); *G01N 27/221* (2013.01)

(58) Field of Classification Search
CPC ...... G01N 33/03; G01N 27/221; G01N 27/22; A47J 37/1271; A47J 37/1223; A47J 37/1266
See application file for complete search history.

(56) References Cited

U.S. PATENT DOCUMENTS

| 4,945,893 | A | 8/1990 | Manchester |
| 5,254,253 | A * | 10/1993 | Behmann .............. C02F 3/1284 210/607 |
| 5,839,360 | A | 11/1998 | Williams |
| 8,497,691 | B2 | 7/2013 | Behle et al. |
| 8,564,310 | B2 | 10/2013 | Yu et al. |
| 9,861,233 | B2 | 1/2018 | McGhee et al. |
| 2007/0227597 | A1* | 10/2007 | Palazzo .................... B67D 7/02 137/565.01 |
| 2008/0282905 | A1* | 11/2008 | Savage ..................... A23L 5/20 99/408 |

(Continued)

FOREIGN PATENT DOCUMENTS

| WO | 2010/148133 A1 | 12/2010 |
| WO | 2017/087361 A1 | 5/2017 |
| WO | 2017-112541 | 6/2017 |

*Primary Examiner* — Farhana A Hoque
(74) *Attorney, Agent, or Firm* — Emerson, Thomson & Bennett, LLC; Roger D. Emerson

(57) ABSTRACT

A system for transporting and measuring the quality of cooking oil exiting a fryer unit using a portable oil transport apparatus. The portable oil transport apparatus has at least one sensor for measuring the quality of oil passing through the system. The portable apparatus may be connected to a storage receptacle for disposing of spent cooking oil, or may be connected back to the fryer unit to reuse the oil, based upon the measured quality of the oil. The portable oil transport apparatus may have an oil filter for filtering out unwanted components contained in the cooking oil. The oil quality sensor is capable of measuring the electrical properties of the oil to determine whether the oil should be reused or disposed of.

20 Claims, 13 Drawing Sheets

(56) References Cited

U.S. PATENT DOCUMENTS

2016/0033463 A1\* 2/2016 Robertson ............. G01N 33/03
　　　　　　　　　　　　　　　　　　　　　　　426/231
2018/0328157 A1\* 11/2018 Bishop .................... E21B 43/26

\* cited by examiner

COOKING OIL FILTRATION TRANSPORT APPARATUS WITH OIL QUALITY SENSOR

TECHNICAL FIELD

The present invention relates generally to an apparatus for disposing of cooking oil. More particularly, the present invention relates to the removal and disposal of cooking oil, or waste oil, from a fryer. Specifically, the present invention relates to a portable receptacle for transporting and/or disposing of cooking oil, independent from the fryer, which may have a sensor for determining the quality of the cooking oil being analyzed and an oil filter for filtering out unwanted products present in the cooking oil.

BACKGROUND

Most, if not all, commercial fryers rely on some sort of oil, often times cooking oil or canola oil, during operation. When the fryer is in operation, the oil experiences gradual degradation over time resulting from use. This degradation results in an overall decrease in the efficiency and effectiveness of the oil for cooking operations. Among those reasons for the lowered effectiveness of the degraded oil include: oxidation and polymerization; cyclic temperature increases; and, hydrolysis.

In order to accurately assess the remaining life of the oil, it becomes necessary to quantify certain properties of the oil in order to determine whether or not the oil is still suitable for use in cooking operations. Several methods for testing the quality of cooking oil exist based upon a number of different properties of the oil. For example, simple means of testing the oil, with relatively unpredictable results, may include evaluating the oil based upon the color, smell, or taste. Slightly more reliable methods of evaluation may include testing the smoke point or viscosity of the oil. While being relatively simple and time effective means of measurement, the results are inherently unreliable and left to the subjective evaluation of the person responsible for administering the test. More reliable means of evaluation therefore rest on certain intrinsic properties of the oil itself.

One particularly useful means of measuring oil quality degradation is to measure the approximate capacitance of the oil, specifically measured by the impurities generated during operation of the fryer. This measurement is referred to as the total polar materials, or TPMs, present in the oil. TPMs are created as a result of the breakup of triglycerides during the frying process into free fatty acids and lipid molecule residues. These substances are able to be measured and classified according to the increased polarity and dielectric constant when compared to that of the original triglycerides in the oil. The result is as follows: when the capacitance measured in the cooking oil increases, the level of TPMs present in the cooking oil has similarly increased.

The use of oil quality sensors for measuring the level of TPMs present in the oil allows for strategic planning and manipulation of the oil throughout a circulation cycle. Additional uses of oil quality sensors may similarly monitor other properties of the oil. For example, a light sensor may be used to monitor the illuminance of the oil or a measure of the polarity of the oil to determine the amount of free fatty acids present.

Accordingly, there is a need in the food service industry for the ability to quickly and effectively remove cooking oil from a fryer following the determination that the oil is no longer suitable for use. A need further exists for the use of oil quality sensors located at positions throughout the oil circulating loop which provide for the most accurate and efficient transport of the oil. Such oil quality sensors may further be operated according to a controller which is capable of determining the relative viability of the used oil and further determining whether or not a particular cycle of oil is capable of being reused, or whether it should be disposed of.

SUMMARY

A system is provided for transporting and measuring the quality of cooking oil used by a fryer. The system involves a fryer vat having at least exit, a storage receptacle having at least one transfer or feed line, and a portable apparatus for the transportation of cooking oil from the fryer vat to the storage receptacle. The portable transport apparatus, or oil caddy, has a storage tank, an opening for receiving cooking oil, and an onboard oil quality sensor for measuring the quality of oil being transferred into the storage tank.

A system is also provided for measuring the quality of oil, having a fryer vat with at least one exit and at least one feed line, a storage receptacle having at least one transfer line or feed line, a feed tank having at least one feed line, and a portable apparatus for the transportation of cooking oil. The portable transport apparatus has a storage tank, a pump having at least one inlet feed and at least one discharge, and an onboard oil quality sensor for measuring the quality of oil passing through the pump, located either on the inlet feed or the discharge, or both. The measure of oil quality may be based upon the TPMs present in the oil, measured according to the relative capacitance of the oil.

A method of transporting oil is also provided. The method of transporting oil begins by allow a fryer vat to deposit oil into a portable transport apparatus. The fryer vat may be allowed to drain directly into the portable transport apparatus, or alternatively utilize a conduit or other similar type of fluid flow pathway in order to transfer cooking oil from the fryer vat to the portable transport apparatus. The portable transport apparatus has a storage tank, a pump having an inlet feed and a discharge, and an onboard oil quality sensor. The portable transport apparatus may also optionally have an oil filter. The oil is then transferred from the fryer vat to the portable transport apparatus. The quality of the oil being transported is measured by the onboard oil quality sensor. The oil quality is then evaluated relative to a predetermined set point. Where the portable transport apparatus contains an oil filter, the oil quality may be measured following filtration of the oil through the oil filter. This evaluation may be performed by a controller which interfaces with the various components in the system to quickly determine whether or not the oil quality is above or below a predetermined set point corresponding to whether or not the oil remains suitable for continued cooking operations.

The discharge of the pump is then connected to a feed line based upon whether or not the measured oil quality is above or below the set point. If the oil quality measurement is below the set point, indicating that the level of TPMs is less than the level required for recycling the oil, the pump may either cease drawing oil from the storage tank, or alternatively the discharge of the pump is connected to a recycle feed loop. The recycle feed loop has an inlet feed from the pump discharge, and optionally an additional inlet feed from a separate feed tank containing a supply of fresh oil, and a fryer vat inlet. Where a fresh oil feed tank is introduced, the fryer vat inlet joins together the inlet feeds from the pump discharge and inlet feed from the feed tank so as to supply the fryer vat with oil through the fryer vat inlet. If the oil quality measurement is above the set point, indicating that the level of TPMs is greater than the level required for disposing of the oil, the oil is transferred to the storage tank of the portable transport apparatus. The portable transport apparatus is then transported to the location of a storage receptacle and the discharge of the pump is connected to a transfer line on the storage receptacle. Oil is then transferred from the storage tank of the portable transport apparatus to the storage receptacle.

An apparatus for transporting oil consists of a storage tank, a pump, an oil filter, and an oil quality sensor. The apparatus is able to be easily moved from location to location, for example by being housed on a frame having wheels. The storage tank may have an opening which allows for oil to be directly dispensed into the storage tank when exiting a fryer unit during cooking operations. The pump has at least one suction line for drawing oil from the storage tank, and at least one discharge for dispensing oil. The discharge line may further contain a return wand, otherwise referred to as a spray wand or dispensing wand, for discharging cooking oil from the storage tank via the pump. The oil filter is placed in the storage tank and removes any unwanted components or products from the oil. The oil quality sensor then measures the quality of the oil to determine whether or not the oil may be reused for further cooking operations, or alternatively should be disposed of by transferring to a storage receptacle. The oil quality sensor may measure electrical properties of the oil, such as measuring the TPMs present in the oil.

BRIEF DESCRIPTION OF THE DRAWINGS

The invention may take physical form in certain parts and arrangement of parts, embodiments of which will be described in detail in this specification and illustrated in the accompanying drawings which form a part hereof and wherein.

DETAILED DESCRIPTION

Figure 1:
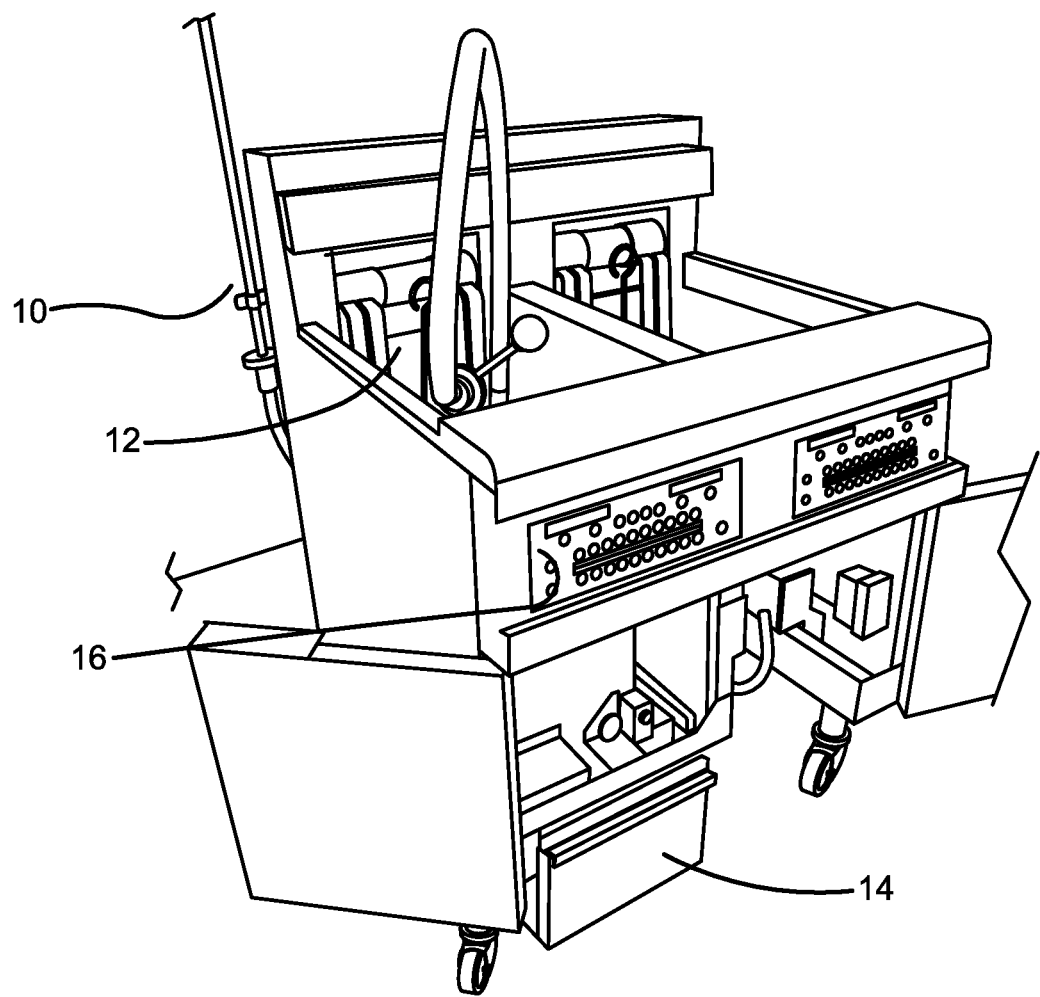
FIG. 1 shows a commercial fryer unit with at least one fryer pot and collection pan.

Referring now to the drawings wherein the showings are for purposes of illustrating embodiments of the invention only and not for purposes of limiting the same, FIG. 1 shows a commercial fryer unit 10 as is common in the food service industry. Located at the top portion of the fryer 10 is a fryer vat 12. The fryer vat 12 is where cooking operations take place. According to the embodiment shown in FIG. 1, a fryer 10 may have multiple fryer vats 12 located in a single unit. Beneath each of the fryer vats 12 may be a receiving pan 14. The fryer vat 12 houses the cooking oil used during operation of the fryer 10. As the oil contained in the fryer vat 12 is subjected to ongoing use, the quality of the oil begins to decrease. Once the oil quality has decreased to a predetermined level corresponding to the useful life of the oil, as identified by any different number of properties used for measuring oil quality, the oil contained within the fryer vat may be referred to as "waste oil." The fryer 10 may include a fryer unit control interface 16 which allows for user control of the cooking operations of the fryer.

Figure 2:
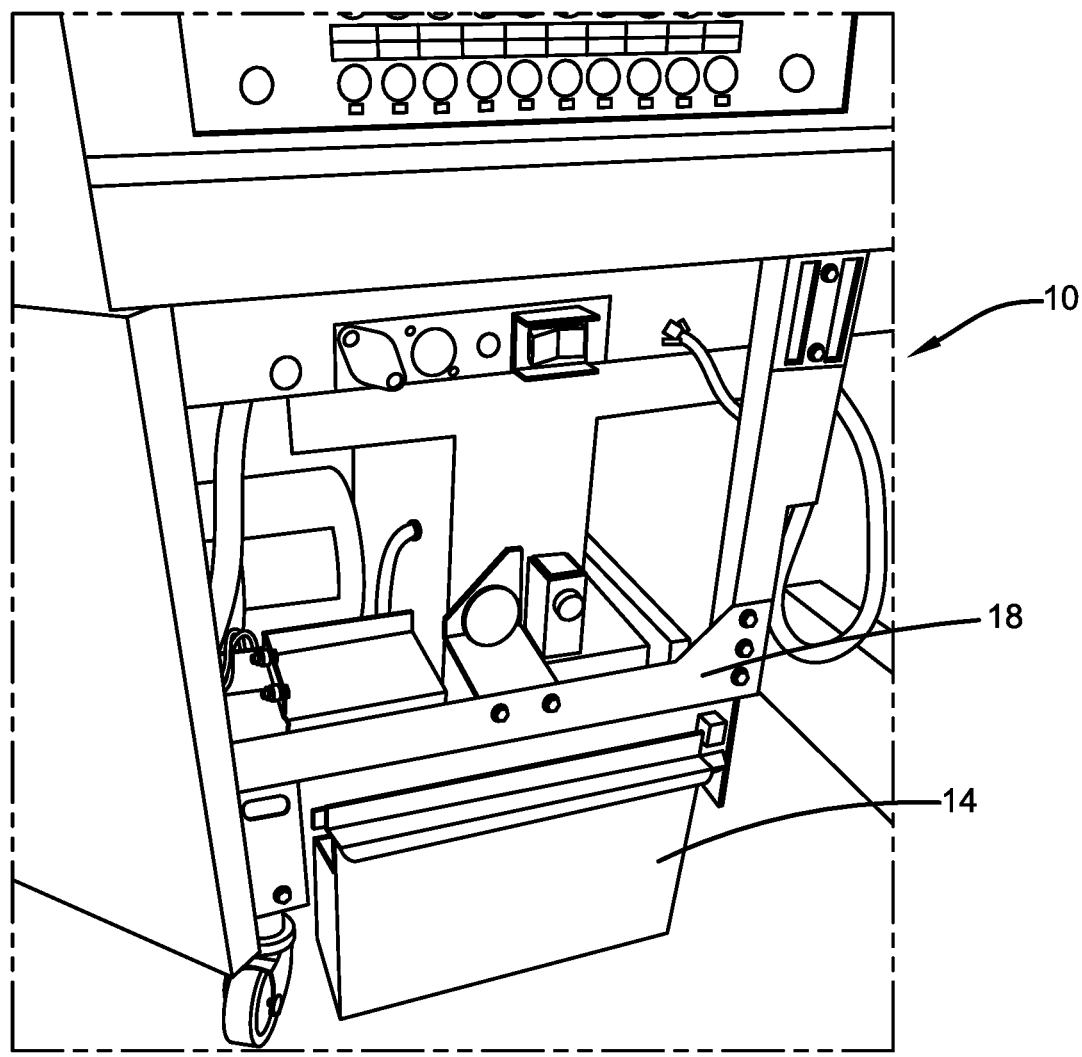
FIG. 2 is an alternative view of a fryer unit showing the collection pan located beneath the fryer pot.
Figure 3:
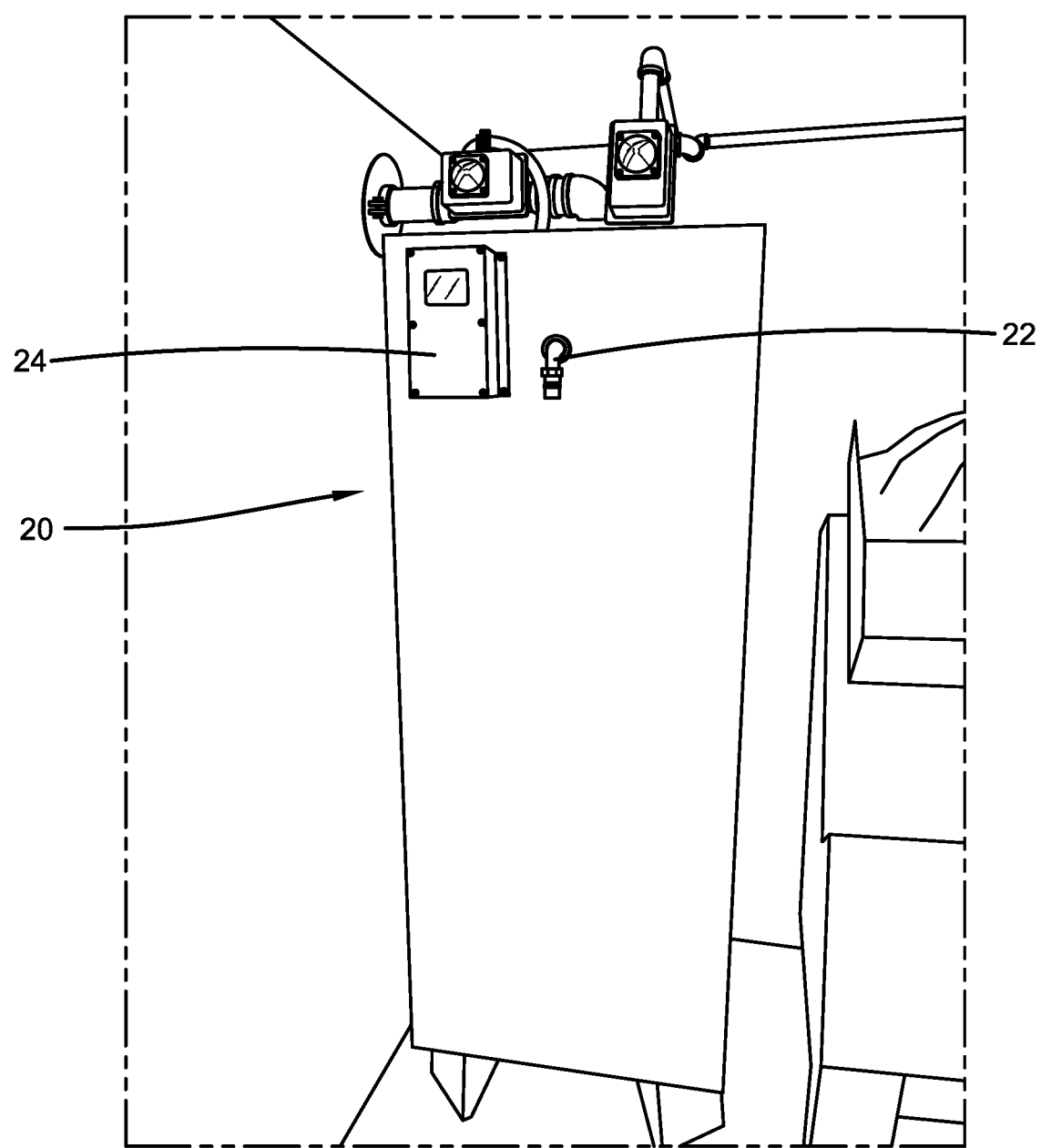
FIG. 3 shows a collection receptacle capable of housing cooking oil.

With reference now to FIG. 2, the receiving pan 14 can be seen positioned about the bottom of the fryer 10 and beneath that of the fryer vat 12. The receiving pan 14 is typically placed inside a housing 18 which provides a secure placement for the receiving pan 14 during operation. When the oil quality has reached a level which requires an exchange of oil, the waste oil is removed from the fryer vat 12 and placed in a storage receptacle 20, as shown in FIG. 3. The storage receptacle 20 may contain at least one inlet 22 through which the cooking oil may be transferred into the storage receptacle 20. A storage receptacle controller 24 may be incorporated into the storage receptacle 20. The storage receptacle controller 24 may be capable of monitoring the level of the cooking oil currently stored, the oil quality of the oil located within the receptacle (such as the TPMs, color of the oil, concentration of free fatty acids ("FFAs"), etc.), or any other properties or characteristics of the oil as desired. The fryer unit control interface 16 may be integrated with that of the storage receptacle controller 24 to further integrate the system.

Many commercial storage receptacles, such as storage receptacle 20 as shown in FIG. 3, are limited with regards to their placement within a kitchen as a result of the overall size and dimensions of the unit. As a result, it can be difficult to run a transfer line from the fryer vat 12 to the storage receptacle 20. It is neither efficient nor practical to run these lines over long distances throughout the kitchen. Instead, portable storage transportation receptacles, sometimes referred to as an "oil caddy," are used as a go-between: the oil is transferred from the fryer vat 12 into the portable storage transportation receptacle; the portable storage transportation receptacle is transported to the stationary storage receptacle; and, the oil is transferred from the portable storage transportation receptacle to the larger, stationary storage receptacle.

Figure 4:
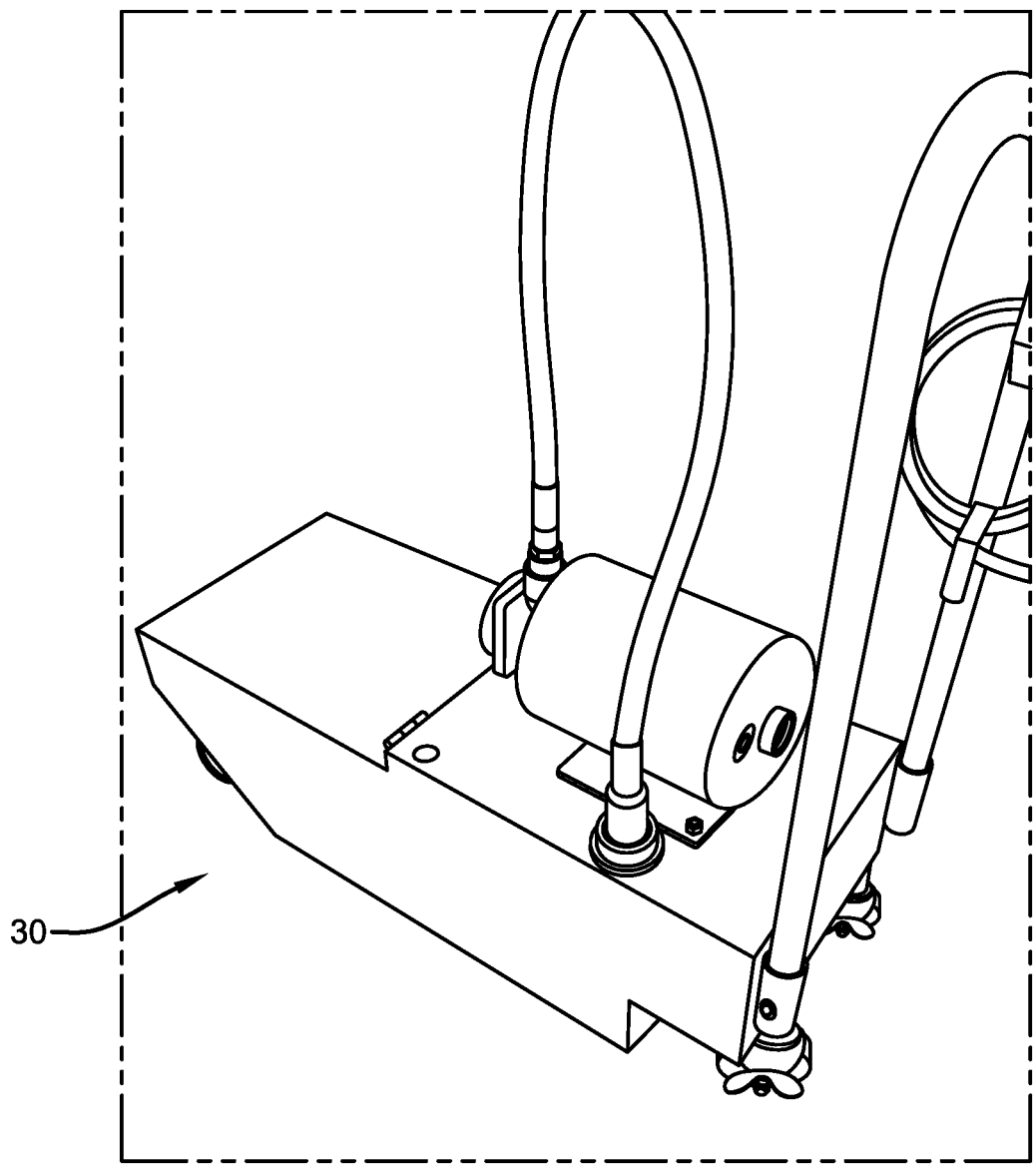
FIG. 4 shows an oil transport apparatus.

FIG. 4 shows an embodiment of a portable storage transportation receptacle, or oil caddy 30. The portable oil caddy 30 allows for the efficient transport of cooking oil from the fryer vat 12 to the storage receptacle 20.

Figure 5:
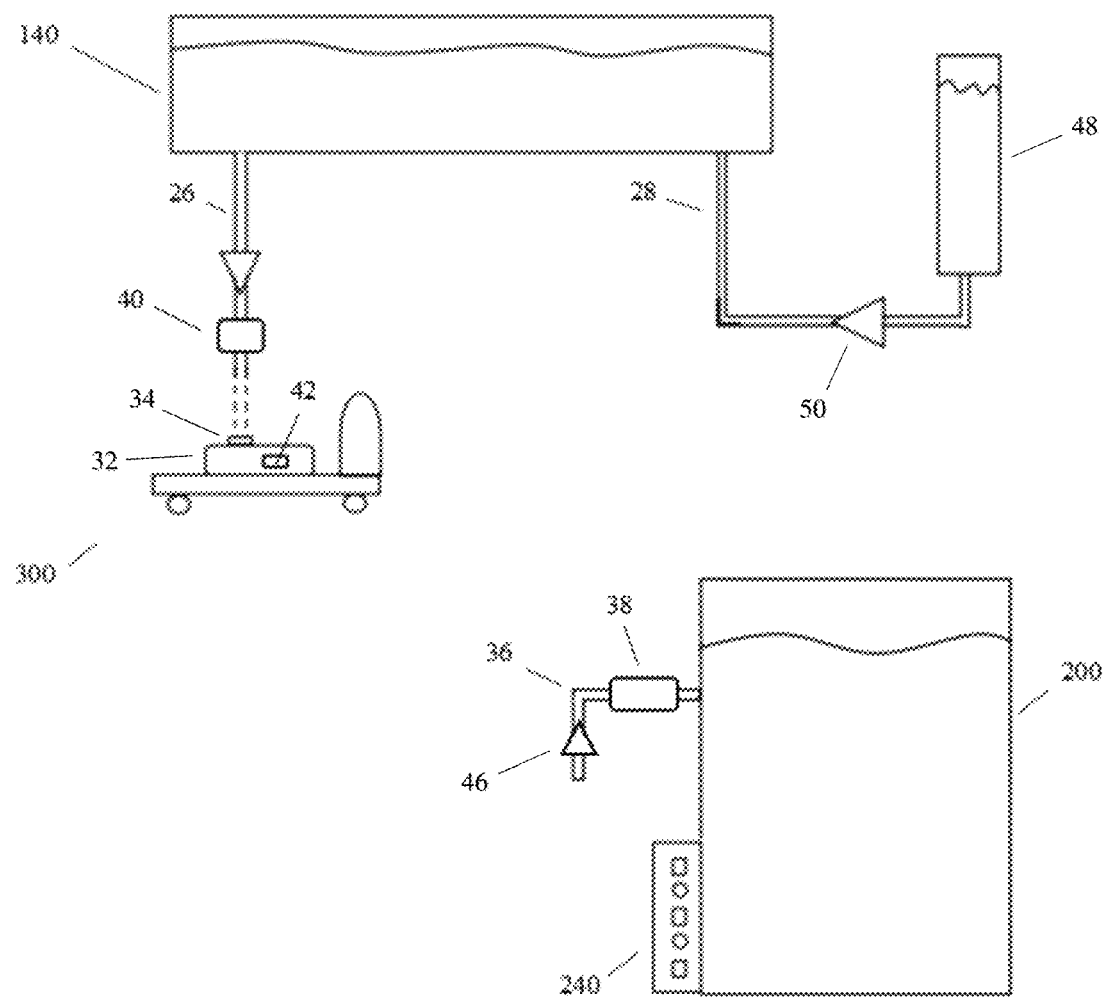
FIG. 5 illustrates an oil changeover loop incorporating an oil transport apparatus.

With reference now to FIG. 5, the fryer vat 140 may contain various exit and hose points for both adding fresh oil and removing cooking oil. According to the embodiment shown in FIG. 5, a drain line 26 allows for oil to travel out of the fryer vat 140. The drain line 26 may be a conventional conduit such as the piping shown in FIG. 5, or alternatively may be any type of opening as identified by those having skill in the art that allows for cooking oil to exit the fryer vat 140. Similarly, the fryer vat 140 may contain a feed line 28 for adding fresh oil to the fryer vat 140. A portable storage transportation receptacle, hereinafter referred to as the oil caddy 300, may be used to transport the cooking oil from the fryer vat 140 to the storage receptacle 200. The oil caddy 300 has a storage tank 32 with at least one opening 34 into which cooking oil may be transferred. The opening 34 may be any type of conventional connection which allows for a hose, line, or other conduit to be connected for the purposes of transferring fluid therebetween, or alternatively a wider opening that allows cooking oil to drain directly from the fryer vat 140 into the storage tank 32. The features and dimensions of the oil caddy 300 may be chosen by those having skill in the art, and are not meant to be limited by those shown in the FIGURES accompanying the present disclosure. The drain line 26 of the fryer vat 140 may be connected to the opening 34 of the oil caddy 300 so as to allow the transfer of oil therebetween.

Once the oil has been transferred from the fryer vat 140 to the oil caddy 300, the oil caddy 300 may be transported to the storage receptacle 200. A transfer line 36 may be used to transfer cooking oil from the oil caddy 300 to the storage receptacle 200. The transfer line may have one end affixed to the oil caddy 300, and a second line affixed to the storage receptacle 200. For example, the transfer line 36 may be permanently or semi-permanently affixed to the oil caddy 300, and then temporarily affixed to the storage receptacle 200 for transfer; alternatively, the transfer line 36 may be permanently or semi-permanently affixed to the storage receptacle 200, and then temporarily affixed to the oil caddy 300 for transfer. A storage receptacle controller 240 may be integrated into the storage receptacle 200. The storage receptacle controller 240 may manage the overall process of storing and transporting the cooking oil, such as monitoring the level of oil in the storage receptacle 200. The storage receptacle 200 may further be fitted with at least one sensor for monitoring the quality of the oil. The oil quality sensor may monitor any different number of properties or characteristics of the oil, such as TPMs, color, FFAs, or any other properties as identified by those having skill in the art.

One useful method for measuring the quality of oil is by way of measuring the electrical properties of the oil, and in particular the dielectric constant. Various types of sensors may be employed to measure such electrical properties, such as a capacitance sensor, open-ended coaxial sensor, conductivity sensor, or a resonant-type sensor. By placing a sensor in any of the various transfer lines throughout the system, the accumulation of polar materials which result from the breakup of fatty acids and lipid molecules in the oil during heating operations may be monitored. This accumulation results in the elevation of the polarity of the oil, which manifests itself as an increase in the dielectric constant of the oil. The sensor thus measures the change in TPMs as the oil travels through the transfer line. The control unit may be programmed with a preset value of TPMs which indicates the proper time to begin an oil changeover based upon whether the oil is suitable for further cooking operations.

According to the embodiment shown in FIG. 5, the oil quality sensor 38 is placed in the transfer line 36 and monitors the quality of the oil entering the storage receptacle 200. Alternative embodiments of the oil quality sensor 38 as shown in FIG. 5 are also possible. The oil quality sensor may be placed at any location through which either cooking oil will travel, such as in a transfer line, or in which static oil will accumulate, such as on the interior of any of the various receptacles used for either transporting or storing the cooking oil. One such embodiment may have an oil quality sensor 40 on the drain line 26 to monitor the quality of the oil as it leaves the fryer vat 140. An alternative embodiment may have an oil quality sensor 42 on the oil caddy 300, either located in the storage tank 32 itself, or alternatively placed about the inlet line characterized by the opening 34. Yet another embodiment may use any different combination of the oil quality sensors 38, 40, and/or 42 to measure the quality of the cooking oil.

A series of control valves may be used to control the flow of oil between the various stages of the system. According to the embodiment shown in FIG. 5, a drain line control valve 44 is placed on the drain line 26. If the drain line 26 is fitted with a drain line oil quality sensor 40, the drain line control valve 44 may be placed either before or after the drain line oil quality sensor 40. A transfer line control valve 46 may be placed on the transfer line 36. If the transfer line 36 is fitted with a transfer line oil quality sensor 38, the transfer line control valve 46 may be placed either before or after the transfer line oil quality sensor 38.

In order to aid either the deposit or draw of oil to or from the oil caddy 300, the oil caddy 300 may be fitted with a pump. Alternatively, a pump may be integrated into the storage receptacle 200 to help draw oil from the oil caddy 300. A controller may be integrated into the system to dictate when to open the various valves, when to measure the oil quality according to the various sensors, when to pump either to or from the oil caddy 300, as well as any other dynamic elements of the oil transfer system.

With continued reference to FIG. 5, as the cooking oil is removed from the fryer vat 140 and transferred to the storage receptacle 200, fresh oil must be introduced to the fryer vat 140 in order to keep the level of oil present in the system at a working level. A fresh oil feed tank 48 may be used to feed fresh oil through the feed line 28 and into the fryer vat 140. A feed line control valve 50 may be fitted on the feed line 28 in order to control the flow of fresh oil from the fresh oil feed tank 48 to the fryer vat 140. The feed line control valve 50 may similarly be integrated into the control system and operated in accordance with the controller. The configuration of the fresh oil feed tank 48 provided in the FIGURES accompanying the present disclosure are provided for purposes of illustration only, and those skilled in the art may use any different number of fresh oil feed sources as are available and known in the art.

Figure 6:
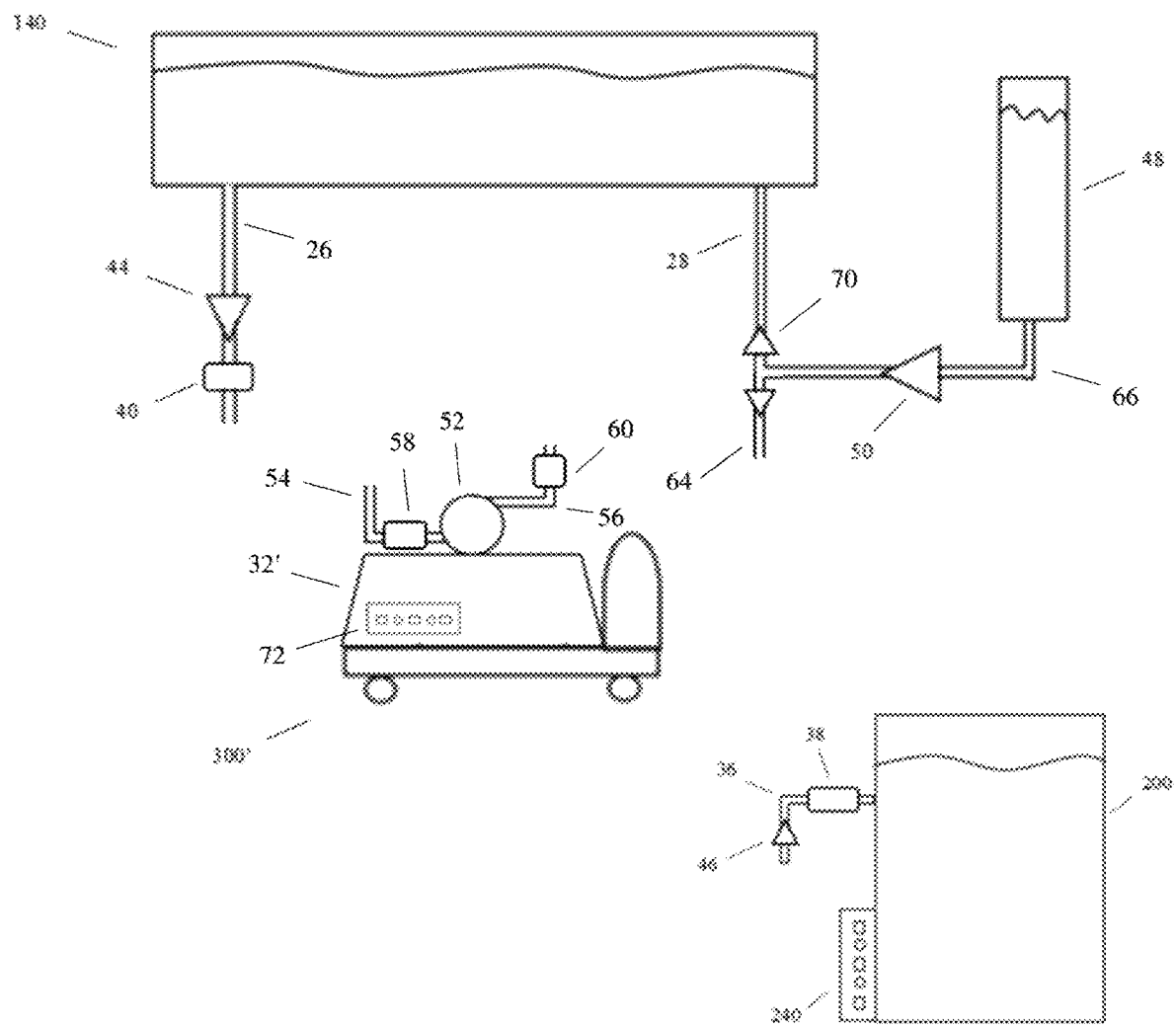
FIG. 6 illustrates an oil changeover filtration loop incorporating an oil transport apparatus.

With reference now to FIG. 6, an alternative embodiment of the oil caddy is shown, oil caddy 300'. The oil caddy 300' is similarly of a portable nature and has a storage tank 32' for storing cooking oil for transport from the fryer vat 140 to the storage receptacle 200. The oil caddy 300' may be fitted with a pump 52 to aid in both the deposit of oil into the storage tank 32', as well as the draw of cooking oil from the storage tank 32' to the storage receptacle 200. The pump 52 may have an inlet feed 54 and a discharge 56. Either, or both, of the inlet feed 54 and discharge 56 may be fitted with an oil quality sensor, 58 and 60, respectively.

According to one embodiment, the oil caddy 300' may be used according to the same procedure as that of the oil caddy 300: cooking oil is transferred from the fryer vat 140 to the storage tank 32' through the drain line 26, with the oil quality being measured by either, none, or both of sensor(s) 40, 48; the oil caddy 300' is transported to the location of the storage receptacle 200; and, the cooking oil is transferred from the storage tank 32' to the storage receptacle 200 through the transfer line 36, with the oil quality being measured by either, none, or both of the oil quality sensors 38, 60. An integrated control system, such as the storage receptacle controller 240, may be used to control the flow of oil out of the vat fry 140 via control valve 44, as well as into the storage receptacle 200 via control valve 46. The pump 52 may be engaged as necessary to aid the flow of oil either into or out of the storage tank 32'.

The oil caddy 300' may also be used to create a filtration loop whereby oil may be recycled back into the fryer vat 140 according to the quality of oil. According to this embodiment, the drain line 26 is hooked into the pump inlet feed 54 and oil is transferred from the fryer vat 140 to the oil caddy 300'. Either, or both, of the oil sensors 40, 58 are used to measure the oil quality of the oil being transferred. If the oil quality is found to be in a suitable range for recycle, then the pump discharge 56 is hooked into the recycle inlet feed 64. If the fresh oil feed tank 48 is located in close proximity to the fryer vat 140, then the pump inlet and exit feeds may be simultaneously hooked into their respective lines and the oil may bypass deposit in the storage tank 32' and be pumped directly through the discharge 56 and into the recycle inlet feed 64. If the fresh feed tank 140 is not located in close proximity to the fryer vat 140, then the oil will be deposited in the storage tank 32' for transport to the location of the recycle inlet feed 64.

With continued reference to FIG. 6, the pump discharge 56 may be fitted with an oil quality sensor 60 to measure the oil quality leaving the oil caddy 300'. Alternatively, or in addition to the oil quality sensor 60, the recycle inlet feed 64 may be fitted with an oil quality sensor to monitor the quality of oil entering the recycle feed. A three-way control valve may then join the flow of the recycle inlet feed 64, feed line 28 into the fryer vat 140, and the exit feed 66 from the fresh oil feed tank 48; a recycle inlet feed control valve 68, a fresh oil feed line control valve 50, and a feed line control valve 70. Based upon the oil quality of oil being introduced into the recycle feed, the control system may open control valve 50 to allow the introduction of fresh oil from the fresh oil feed tank 48 into the recycle feed. Upon the mixture of recycled oil from the recycle inlet feed 64 and fresh oil from the fresh oil feed tank exit feed 66, feed line control valve 70 may be opened to return the oil to the fryer vat 140 via feed line 28.

According to one embodiment, the oil caddy 300' may have an onboard controller which may be integrated into the control system. Based upon the measured oil quality either entering or exiting the oil caddy 300', the onboard controller may direct the operation of the various stages of either the recycle or disposal cycle. According to one embodiment, a predetermined set point is chosen which indicates the level of TPMs at which oil is determined to no longer be viable for cooking operations. When an oil quality sensor measures the TPM level to be above this set point, the system is alerted that the oil is no longer suitable for cooking operations, and the appropriate control valves are opened/closed in order to dictate the flow of cooking oil accordingly such that it may be stored in the storage tank 32' of the oil caddy 300'. When an oil quality sensor measures the TPM level to be below this set point, the system is alerted that the oil is still suitable for cooking operations, and the appropriate control valves are opened/closed in order to dictate the flow of oil accordingly such that it may be pumped through the oil caddy 300' and into the recycle feed.

Figure 7:
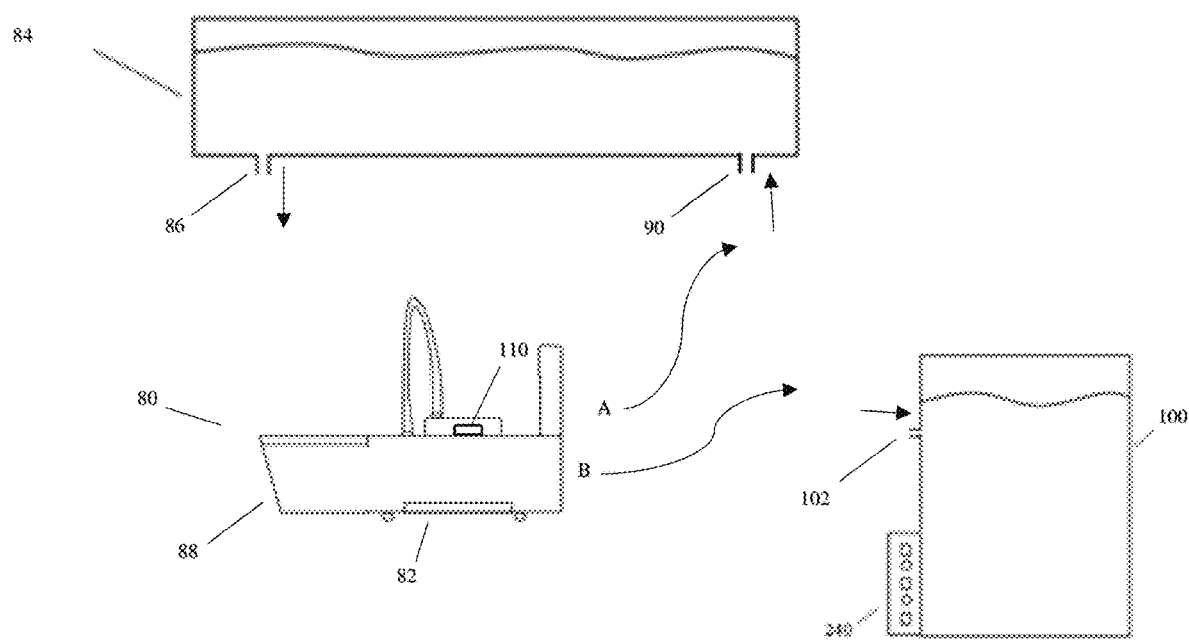
FIG. 7 illustrates a portable filtration cooking oil transportation apparatus.

With reference now to FIG. 7, and alternative embodiment of the portable apparatus for the transportation of cooking oil is shown, oil caddy 80. Oil caddy 80 differs from the previous embodiments of the oil caddy, oil caddies 30, 300, and 300', in that oil caddy 80 may further be equipped with an onboard oil filter 82. The onboard oil filter 82 allows for the cooking oil transferred from the fryer unit 84 to be filtered so as to recycle or reuse some, or all, of the cooking oil. According to the embodiment shown in FIG. 7, cooking oil is transferred from the fryer unit 84 through a discharge 86. The discharge may be a conventional discharge line or piping. However, alternative embodiments may utilize a gravity drain discharge which transfers the cooking oil from the fryer unit 84 into the storage tank 88 of oil caddy 80. For example, referring back to FIG. 1, oil caddy 80 may be positioned underneath the fryer unit 10 such that storage tank 88 is in place of the receiving pan 14, thereby allowing the cooking oil to drain directly into the storage tank 88. The storage tank 88 may have a large opening capable of directly receiving the cooking oil from the fryer unit, thereby functioning as the fryer vat itself during cooking oil collection.

Inside the storage tank 88 may be inserted at least one onboard oil filter 82. While the cooking oil is stored in the storage tank 88, the cooking oil is cycled through the onboard oil filter 82. Once the oil has been sufficiently filtered, for example following a specified number of passes through the filter or the passage of an allotted period of time, the oil contained in the storage tank 88 may be suitable for recycling back into the fryer unit 84 for continued use in cooking operations. The oil filter 82 may be any device capable of filtering out any unwanted components of the cooking oil in order to render the oil suitable for continued use in cooking operations.

Figure 8:
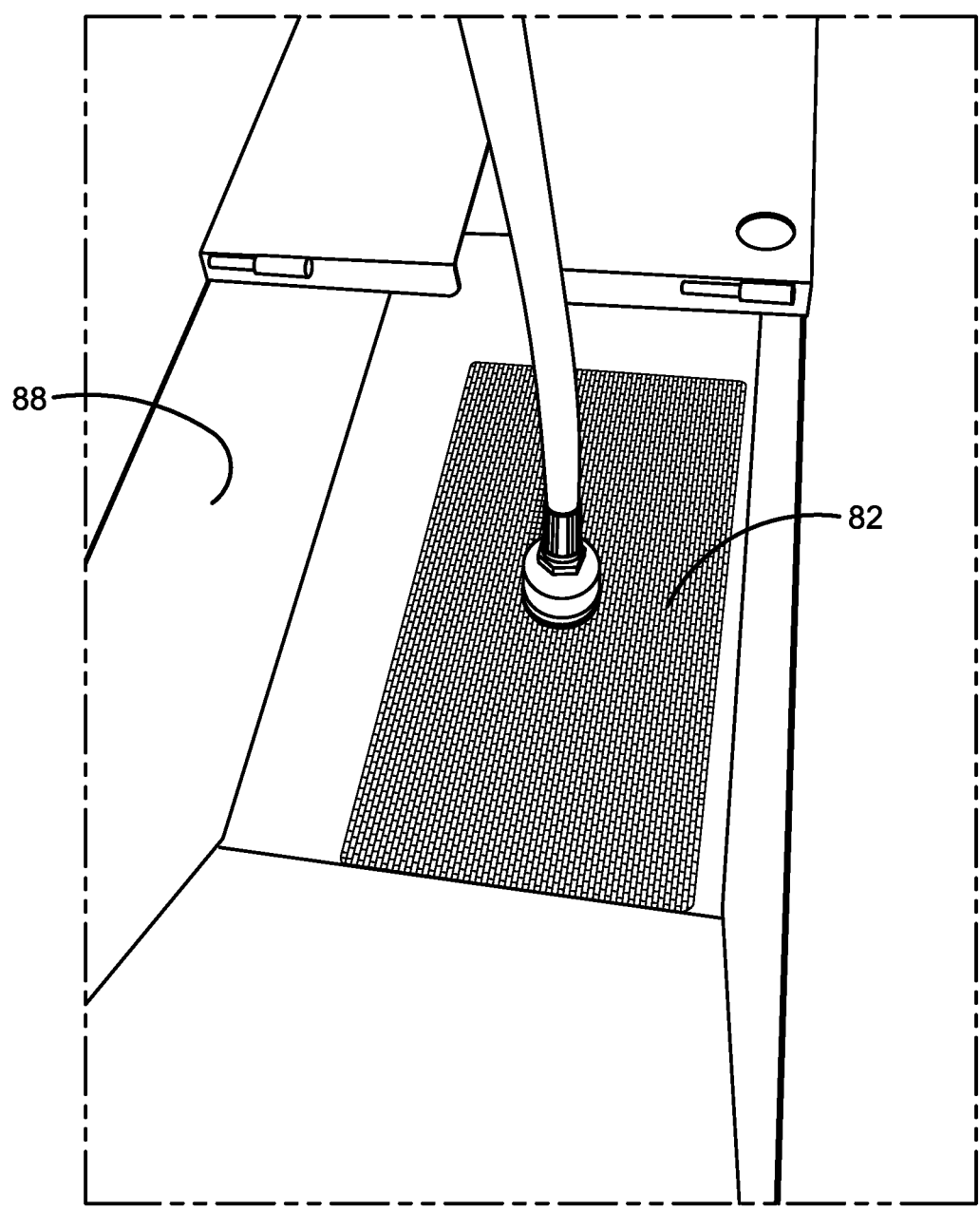
FIG. 8 shows an oil filter placed inside the storage tank of a portable filtration cooking oil transportation apparatus.
Figure 9:
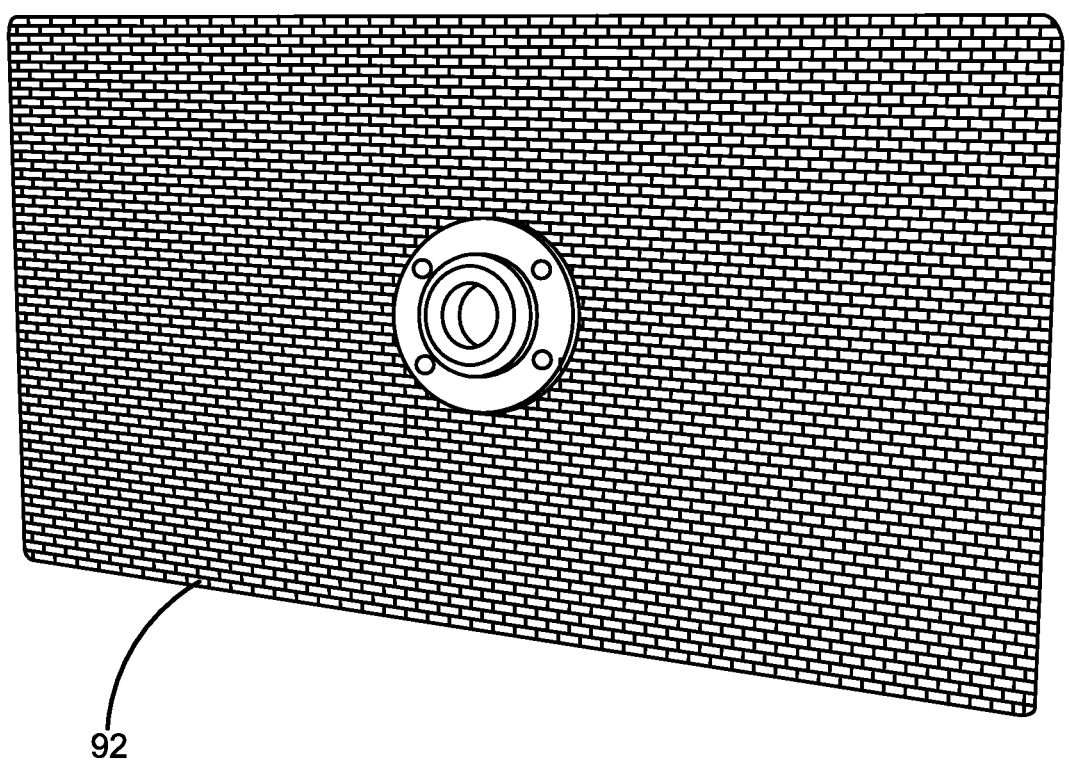
FIG. 9 is one embodiment of an oil filter.
Figure 10:
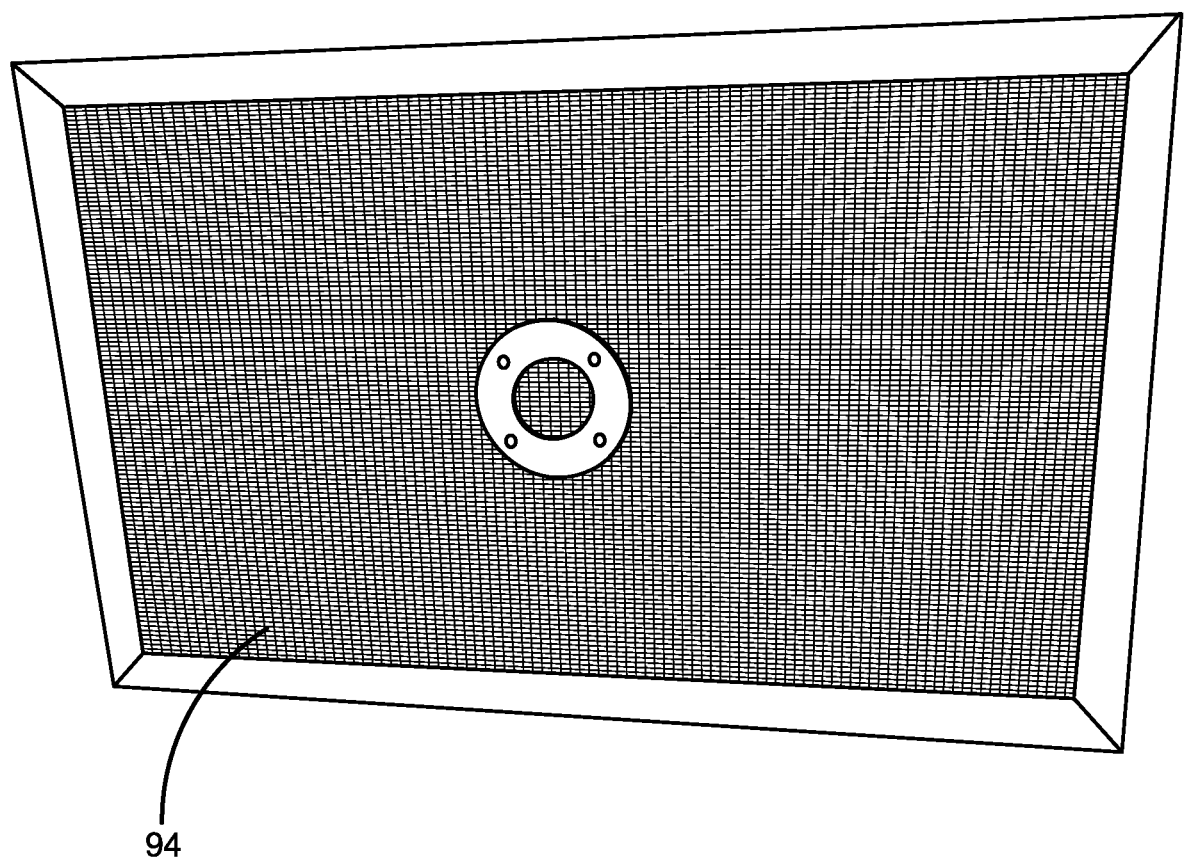
FIG. 10 is an alternative embodiment of an oil filter.
Figure 11:
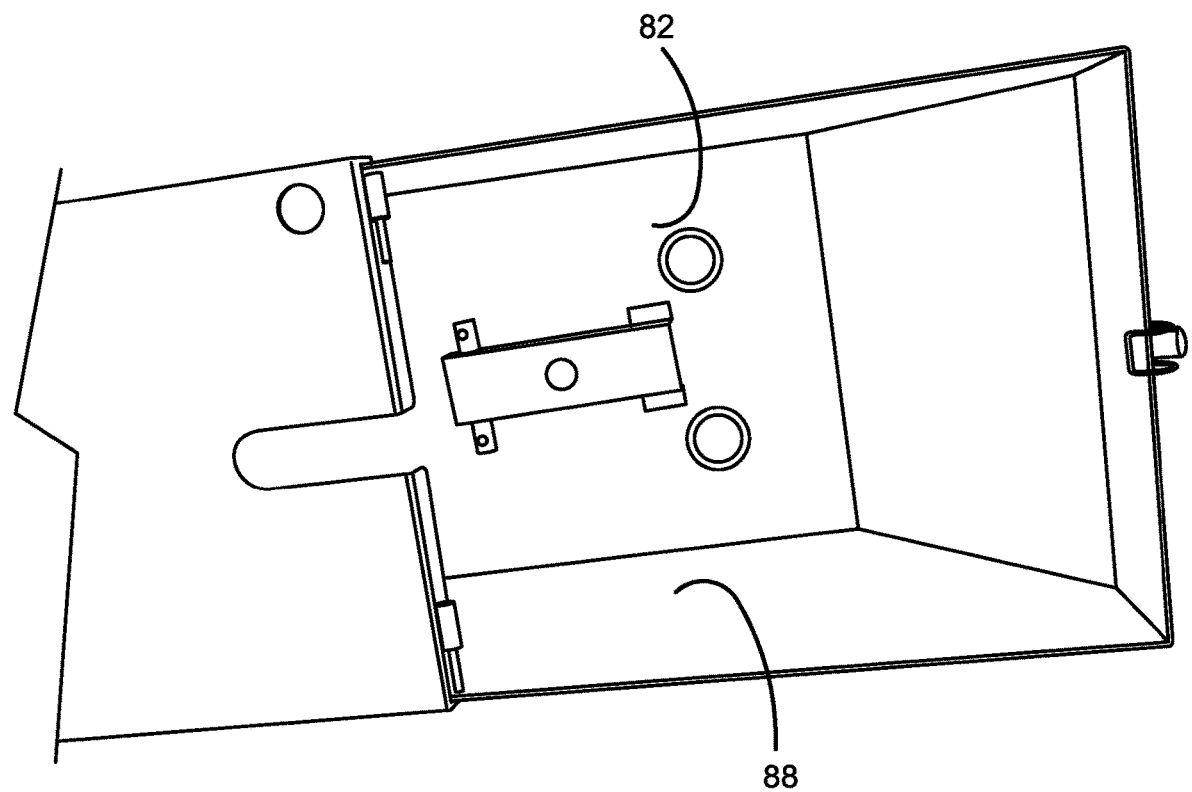
FIG. 11 is an alternative embodiment of an oil filter placed inside the storage tank of a portable filtration cooking oil transportation apparatus.

With reference to FIG. 8, oil filter 82 is shown placed inside the storage tank 88. Referring now to FIG. 9, one example of an oil filter is shown, waffled filter 92. Waffled filter 92 contains a cross-pattern design which allows for oil to pass through while trapping any unwanted components contained in the cooking oil. Waffled filter 92 may be constructed of stainless steel to provide a filter which is reusable. Waffled filter 92 may be used in conjunction with a filter paper placed over top, such as a paper filter. With reference now to FIG. 10, a screened filter 94 may be used. Screened filter 94 may be comprised of a mesh or other similar type of netting or covering in order to filter out the unwanted components of the cooking oil. Screened filter 94 may also be used in conjunction with that of waffled filter 92, with waffled filter 92 being placed inside that of the screened filter 94. Various other types of oil filters may be used in the storage tank 88 as identified by those having skill in the art. With reference now to FIG. 11, a carbon filter 106 is shown placed in the storage tank 88. The carbon filter 106 may provide greater filtration properties, as readily understood by those having skill in the art, and may be placed in the base of the storage tank 88. As cooking oil is circulated through the storage tank 88, the oil filter will continuously remove unwanted components from the cooking oil.

Figure 12:
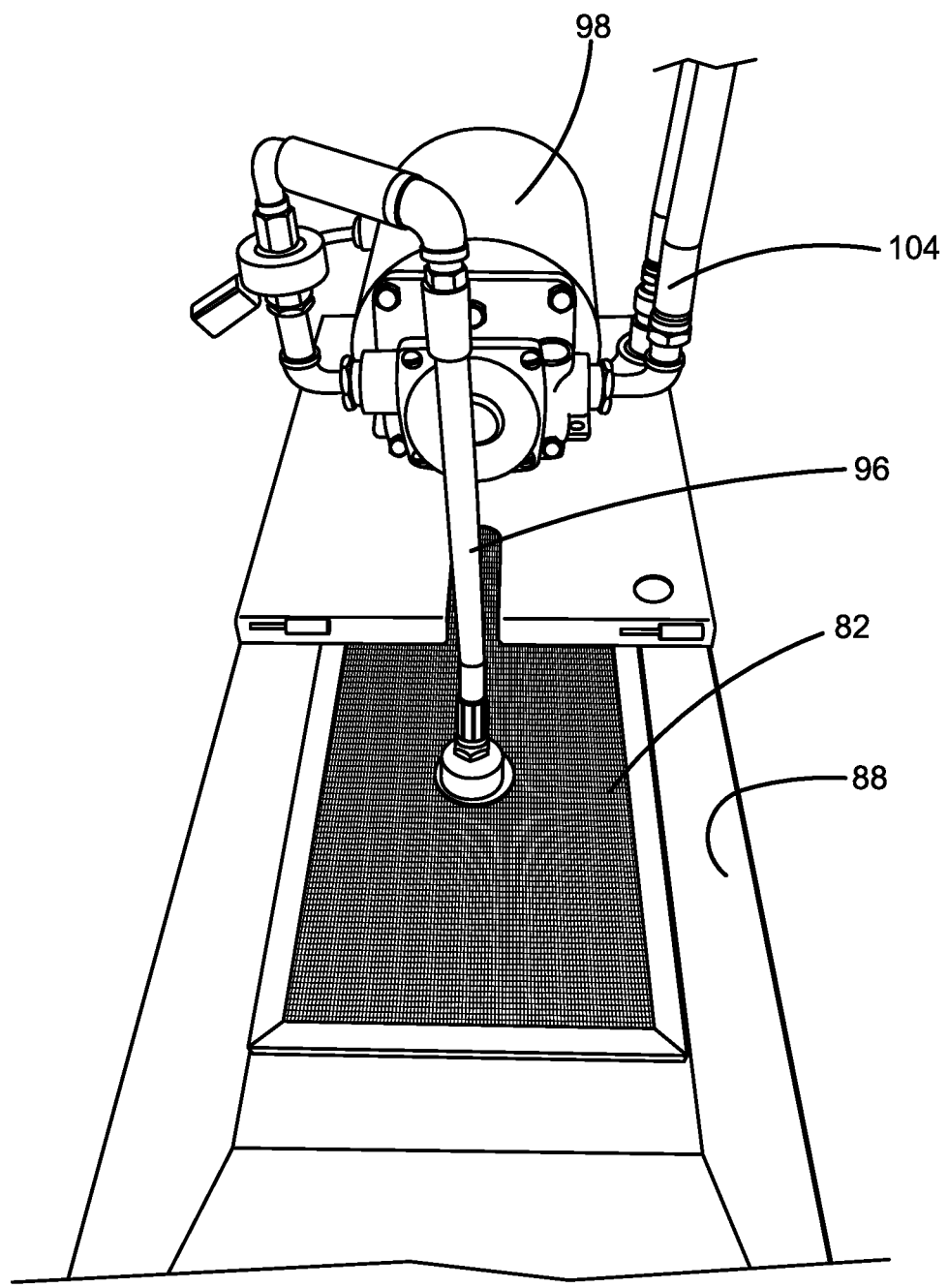
FIG. 12 illustrates the configuration of a pump on a portable filtration cooking oil transportation apparatus; and, FIG. 13 illustrates the configuration of a pump on a portable filtration cooking oil transportation apparatus fitted with a return wand.

With reference now to FIGS. 7 and 12, oil caddy 80 is shown configured to transfer filtered oil from the storage tank 88 to a housing receptacle, such as back to the fryer unit 84 for reuse, or to the storage receptacle 100 for storage and ultimately disposal. Oil caddy 80 may be equipped with at least one onboard oil quality sensor capable of measuring the relative quality of the oil, such as oil quality sensor 110. Oil caddy 80 may further be equipped with at least one controller integrated with a control system. Upon measuring the quality of oil contained in the storage tank 88 by oil quality sensor 110, this oil quality is evaluated in order to determine whether or not the oil is suitable for continued use in cooking operations. If oil quality sensor 110 is a TPM sensor, then a measured TPM value above that corresponding to oil suitable for continued use will result in oil caddy 80 following path A, wherein oil caddy 80 is transported to the location of the inlet to the fryer unit 84, the discharge of oil caddy 80 is connected to fryer unit inlet 90, and oil is transferred from the storage tank 88 to the fryer unit 84. If a measured TPM value is below that corresponding to oil suitable for continued use, oil caddy 80 follows path B, wherein oil caddy 80 is transported to the location of the inlet to the storage receptacle 100, the discharge of oil caddy 80 is connected to storage receptacle inlet 102, and oil is transferred from the storage tank 88 to the storage receptacle 100.

According to one embodiment, the storage tank 88 may be fitted with an in-vat oil quality sensor, such as a sensor capable of measuring the TPMs in the oil. According to such an embodiment, such as that shown in FIG. 7, the in-vat oil quality sensor provides a measure of the quality of the oil contained in the storage tank after filtration. If the oil quality is deemed to still be suitable for use in cooking operations, oil caddy 80 may be configured to recycle the oil back to the fryer unit 84 via fryer unit inlet 90. If the oil quality is deemed no longer suitable for cooking operations, oil caddy 80 is transported to the location of the storage receptacle 100 and the cooking oil is transported into the storage receptacle 100 through storage receptacle inlet 102.

Turning now to FIG. 12, the filtered oil must be drawn from the storage tank 88. According to one embodiment, first pump line 96 is connected to a corresponding receiving port on the oil filter 82 placed inside storage tank 88 and acts as a suction line. First pump line 96 draws the filtered oil by way of onboard pump 98. The filtered oil will then exit through second pump line 104, which may be configured to the inlet of an oil housing receptacle, such as the fryer unit 84 or storage receptacle 100, acting as a discharge line, in order to deposit the filtered oil in the desired location. According to an alternative embodiment, second pump line 104 acts as a suction line, drawing filtered oil by way of onboard pump 98. The filtered oil then exits through first pump line 96, which may be configured to the inlet of either the fryer unit 84 or storage receptacle 100, acting as a discharge line, in order to deposit the filtered oil in the desired location.

Oil caddy 80 may have at least one inline oil quality sensor. The inline oil quality sensor may be placed in either the first pump line 96 or the second pump line 104, or both. The inline oil quality sensor measures the quality of oil as it passes through the respective line in which the sensor is placed. The inline oil quality sensor may be a TPM sensor capable of monitoring the dielectric constant of the oil as it travels through the respective line in which the sensor is placed. When configured according to such an embodiment, oil caddy 80 is capable of functioning as a traditional portable cooking oil transportation receptacle, or alternatively as a portable oil filtration system, allowing cooking oil to be transported directly into the storage tank 88, filtered through oil filter 82, the quality of the oil measured by oil an quality sensor, and recycled back into the fryer unit 84.

Figure 13:
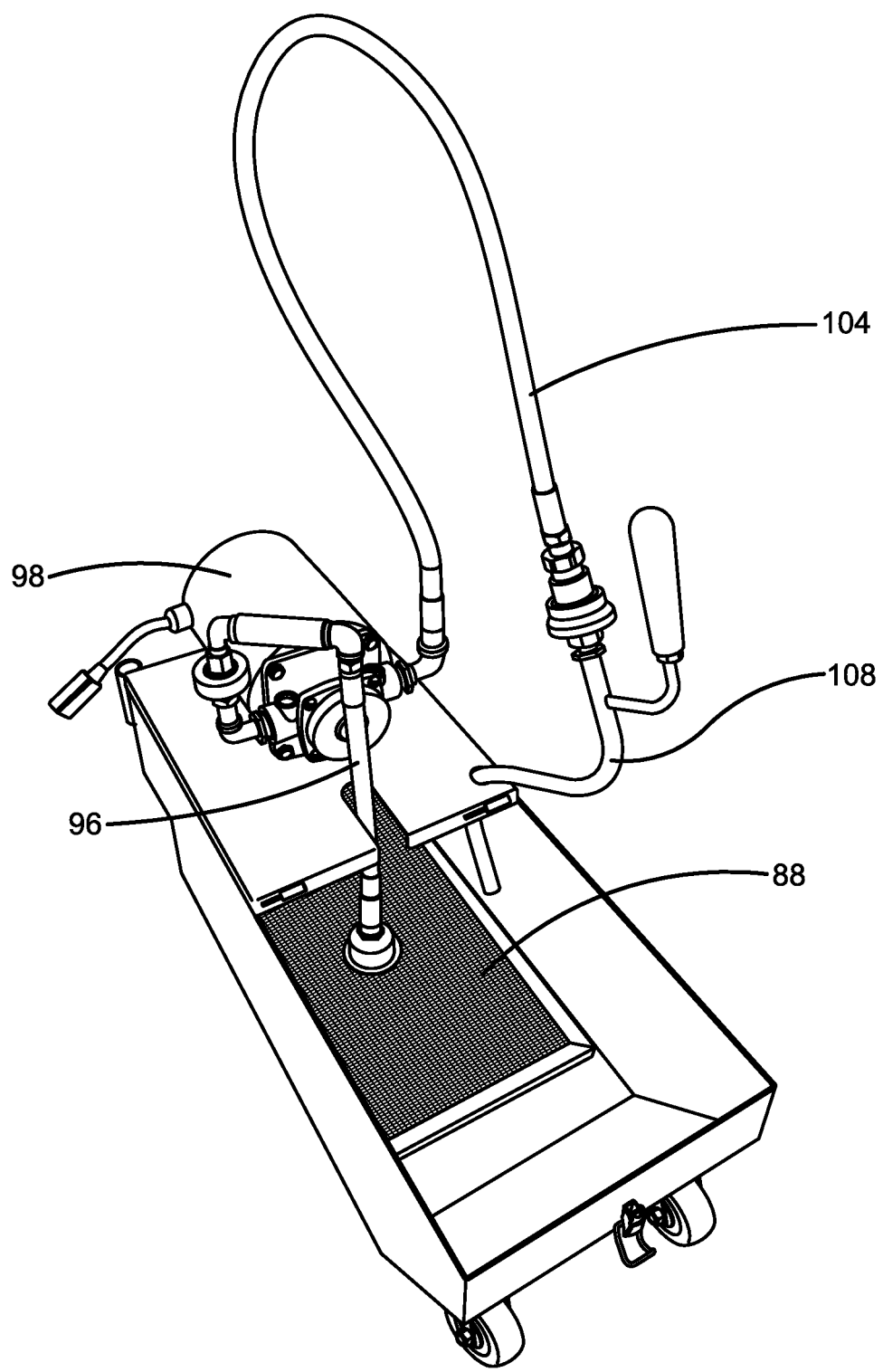

With reference now to FIG. 13, oil caddy 80 may be configured to support a return wand 108. Return wand 108, otherwise referred to as a dispensing wand or spray wand, allows for the dispensing of cooking oil through the discharge of the pump 98. Return wand 108 is configured directly to the end of the pump discharge line and provides the ability to easily manipulate the line in order to provide greater maneuverability of the end location of the dispensed oil. According to one embodiment, the return wand 108 may be inserted back into the storage tank 88 so as to allow the cooking oil to cycle through the storage tank. This embodiment may place an oil quality sensor on either of the respective pump lines (i.e., suction or discharge) for measuring the quality of oil being cycled through the pump 92 in the storage tank 88. Alternatively, the return wand 108 may be directed to any different number of desired locations in order to manipulate the flow of cooking oil being dispensed through the discharge line 104 of the pump 98.

As described above, the present disclosure has been described in association with various aspects thereof and it is understood that many changes and modifications to the described aspects can be carried out without departing from the scope and the spirit of the present disclosure that is intended to be limited only by the appended claims.

Having thus described the invention, it is now claimed:

1. An apparatus for transporting oil, comprising:
a storage tank for receiving oil;
a pump having at least one suction line for drawing oil and at least one discharge for dispensing oil,
an oil quality sensor for measuring the quality of oil received in the storage tank; and
a controller for evaluating the oil quality measured by the oil quality sensor and determining if it is above or below a predetermined set point and transporting the apparatus to the location of a housing receptacle based upon the measured oil quality, where:
if the oil quality relative to the set point indicates continued use for cooking operations: transporting the apparatus to the location of a fryer unit, connecting the discharge of the pump to the inlet of the fryer unit, and transferring the oil from the storage tank of the apparatus to the fryer unit; or,
if the oil quality relative to the set point indicates disposal of the oil: transporting the apparatus to the location of a storage receptacle, connecting the discharge of the pump to the inlet of the storage receptacle and transferring the oil from the storage tank of the apparatus to the storage receptacle.

2. The apparatus of claim 1, further comprising an oil filter located in the storage tank.

3. The apparatus of claim 2, wherein the oil quality sensor measures the quality of filtered oil.

4. The apparatus of claim 1, wherein the oil quality sensor is an in-vat oil quality sensor.

5. The apparatus of claim 1, further comprising a frame designed to transport the apparatus as a single unit from one location to another.

6. The apparatus of claim 1, wherein the oil quality sensor is an inline oil quality sensor located in the discharge of the pump.

7. The apparatus of claim 1, wherein the discharge further comprises a return wand for dispensing oil.

8. The apparatus of claim 4, wherein the oil quality sensor is a TPM sensor.

9. An apparatus for transporting oil, comprising:
a storage tank for receiving oil, wherein the storage tank has an opening designed to receive oil directly from a fryer unit during cooking operations;
a pump having at least one suction line for drawing oil and at least one discharge for dispensing oil;
an oil filter located in the storage tank;
an oil quality sensor for measuring the quality of oil received in the storage tank; and
a controller for evaluating the oil quality measured by the oil quality sensor and determining if it is above or below a predetermined set point and transporting the apparatus to the location of a housing receptacle based upon the measured oil quality, where:
if the oil quality relative to the set point indicates continued use for cooking operations: transporting the apparatus to the location of a fryer unit, connecting the discharge of the pump to the inlet of the fryer unit, and transferring the oil from the storage tank of the apparatus to the fryer unit; or, if the oil quality relative to the set point indicates disposal of the oil: transporting the apparatus to the location of a storage receptacle, connecting the discharge of the pump to the inlet of the storage receptacle, and transferring the oil from the storage tank of the apparatus to the storage receptacle.

10. The apparatus of claim 9, wherein the oil quality sensor is located in the storage tank.

11. The apparatus of claim 9, wherein the oil quality sensor is an inline sensor located in the discharge of the pump.

12. The apparatus of claim 9, wherein the discharge of the pump further comprises a return wand for dispensing oil.

13. A method of transporting oil, comprising the steps of:
gathering oil in an oil transport apparatus, said oil transport apparatus comprising:
a storage tank for receiving oil;
a pump having at least one suction line for drawing oil and at least one discharge for dispensing oil, and;
an oil quality sensor;
measuring the quality of oil in the apparatus;
evaluating the oil quality measured by the oil quality sensor and determining if it is above or below a predetermined set point; and,
transporting the oil transport apparatus to the location of a housing receptacle based upon the measured oil quality, where:
if the oil quality relative to the set point indicates continued use for cooking operations: transporting the oil transport apparatus to the location of a fryer unit, connecting the discharge of the pump to the inlet of the fryer unit, and transferring the oil from the storage tank of the oil transport apparatus to the fryer unit; or, if the oil quality relative to the set point indicates disposal of the oil: transporting the oil transport apparatus to the location of a storage receptacle, connecting the discharge of the pump to the inlet of the storage receptacle, and transferring the oil from the storage tank of the oil transport apparatus to the storage receptacle.

14. The method of claim 13, wherein the oil transport apparatus further comprises an oil filter located in the storage tank.

15. The method of claim 14, further comprising the step of filtering the oil through the oil filter in the storage tank.

16. The method of claim 13, wherein the step of evaluating the oil quality is performed by a controller.

17. The method of claim 16, wherein the controller interfaces with the oil transport apparatus, storage receptacle, and fryer unit.

18. The method of claim 13, wherein the discharge of the pump further comprises a return wand for dispensing oil.

19. The method of claim 13, wherein the oil quality sensor is a TPM sensor, and the step of evaluating the quality of the oil comprises comparing the measured level of TPMs in the oil to a predetermined TPM value.

20. The method of claim 13, wherein the step of gathering oil in the oil transport apparatus further comprises placing the storage tank of the oil transport apparatus directly below a fryer unit used for cooking operations such that cooking oil used by the fryer unit deposits directly into the storage tank.

\* \* \* \* \*